(12) United States Patent
Muntoni et al.

(10) Patent No.: US 10,947,538 B2
(45) Date of Patent: Mar. 16, 2021

(54) ALLELE-SPECIFIC GENE SUPPRESSION

(71) Applicant: UCL BUSINESS LTD, London (GB)

(72) Inventors: Francesco Muntoni, London (GB); Haiyan Zhou, London (GB); Mary Reilly, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 16/083,703

(22) PCT Filed: Mar. 8, 2017

(86) PCT No.: PCT/GB2017/050624
§ 371 (c)(1),
(2) Date: Sep. 10, 2018

(87) PCT Pub. No.: WO2017/153753
PCT Pub. Date: Sep. 14, 2017

(65) Prior Publication Data
US 2019/0144869 A1    May 16, 2019

(30) Foreign Application Priority Data

Mar. 11, 2016 (GB) .................................. 1604261.6

(51) Int. Cl.
*A61K 48/00* (2006.01)
*C12N 15/11* (2006.01)
(Continued)

(52) U.S. Cl.
CPC .... *C12N 15/1137* (2013.01); *C12Y 203/0105* (2013.01); *C12N 2310/11* (2013.01); *C12N 2310/122* (2013.01); *C12N 2310/14* (2013.01); *C12N 2310/20* (2017.05); *C12N 2310/315* (2013.01); *C12N 2310/321* (2013.01);
(Continued)

(58) Field of Classification Search
CPC .............. C12N 15/113; C12N 15/1137; C12N 2310/11; C12N 2310/14; C12N 2310/20; C12N 2310/122; C12N 2310/315; C12N 2310/321; C12N 2310/322;
(Continued)

(56) References Cited

FOREIGN PATENT DOCUMENTS

WO    2004/013280 A2    2/2004

OTHER PUBLICATIONS

Michaela Auer-Grumbach (Orphanet Journal of Rare Diseases 2008, vol. 3:pp. 1-7).*
(Continued)

*Primary Examiner* — Terra C Gibbs
(74) *Attorney, Agent, or Firm* — Kilpatrick Townsend & Stockton LLP

(57) ABSTRACT

The invention relates to an oligonucleotide that supresses the expression of an allele carrying a dominant mutation that causes hereditary sensory neuropathy type I (HSN1), wherein the suppression takes place through hybridisation of said oligonucleotide to the DNA of said allele or to an RNA transcript of said allele, and which either does not suppress the expression of a wild-type allele not containing the dominant mutation or suppresses the expression of said wild-type allele to a lesser extent than it suppresses the expression of the dominant mutant allele; and also pharmaceutical compositions comprising oligonucleotides of the invention and treatments of HSN1 using such oligonucleotides.

14 Claims, 6 Drawing Sheets
Specification includes a Sequence Listing.

(51) Int. Cl.
 C07H 21/02 (2006.01)
 C07H 21/04 (2006.01)
 C12N 15/113 (2010.01)
(52) U.S. Cl.
 CPC ......... C12N 2310/322 (2013.01); C12N 2310/3231 (2013.01); C12N 2310/341 (2013.01); C12N 2310/3521 (2013.01); C12N 2310/3533 (2013.01); C12N 2320/34 (2013.01)
(58) Field of Classification Search
 CPC ...... C12N 2310/3231; C12N 2310/341; C12N 2320/34
 See application file for complete search history.

(56) References Cited

OTHER PUBLICATIONS

International Search Report issued in connection with corresponding International Application No. PCT/GB2017/050624, dated May 30, 2017, 2 pages.
Bode et al., "*HSAN1 mutations in serine palmitoyltransferase reveal a close structure-function-phenotype relationship*", Human Molecular Genetics, vol. 25, No. 5, Dec. 17, 2015, pp. 853-865.
Bolduc et al., "*siRNA-mediated Allele-specific Silencing of a COL6A3 Mutation in a Cellular Model of Dominant Ullrich Muscular Dystrophy*", Molecular Therapy: Nucleic Acids (2014) 3, e147.
Courtney et al., "*siRNA Silencing of the Mutant Keratin 12 Allele Limbal Epithelial Cells Grown from Patients with Meesmann's Epithelial Corneal Dystrophy*", IOVS (2014), 55, pp. 3352-3360.
Dedov et al., "*Activity of partially inhibited serine palmitoyltransferase is sufficient for normal sphingolipid metabolism and viability of HSN1 patient cells*", Biochimica et Biophysica Acta, vol. 1688, No. 2, Mar. 2, 2004, pp. 168-175.
Eichler et al., "*Overexpression of the wild-type SPT1 subunit lowers desoxysphingolipid levels and rescues the phenotype of HSAN1*", Journal of Neuroscience, vol. 29, No. 46, Nov. 18, 2009, pp. 14646-14651.
Hornemann et al., "*A systematic comparison of all mutations in hereditary sensory neuropathy type I (HSAN I) reveals that the G387A mutation is not disease associated*", Neurogenetics, vol. 2, 2009, 10: 135-143.
Monteys et al., "*Artificial miRNAs Targeting Mutant Hungtingtin Show Preferential Silencing in vitro and in vivo*", Molecular Therapy: Nucleic Acids (2015) vol. 4, e234.
Murray et al., "*Allele-specific inhibition of Rhodopsin with an antisense oligonucleotide slows photoreceptor cell degeneration*", Investigative Opthalmology & Visual Science, vol. 56, No. 11, Oct. 5, 2015, p. 6362.
Sarajarvi et al., "*Developing allele-specific gene silencing as a therapeutic strategy for hereditary sensory neuropathy type I*", Neuromuscular Disorders (2016) 26SI, p. 74 Abstract.
Takahashi et al., "*A novel measurement of allele discrimination for assessment of allele-specific silencing by RNA interference*", Molecular Biology Reports (2014), 41:7115-7120.
Wiles et al., "*CRISPR-Cas9-mediated genome editing and guide RNA design*", Mammalian Genome (2015), 26: 501-510.

\* cited by examiner

ALLELE-SPECIFIC GENE SUPPRESSION

CROSS-REFERENCE TO RELATED APPLICATIONS

This application is a national stage application under 35 U.S.C. § 371 of International Patent Application No. PCT/GB2017/050624, filed Mar. 8, 2017, which claims priority to GB Patent Application No. 1604261.6, filed Mar. 11, 2016, the disclosures of which are hereby incorporated by reference in their entirety for all purposes.

FIELD OF THE INVENTION

The invention relates to oligonucleotides capable of supressing an allele carrying a dominant mutation. Further, the invention also relates to oligonucleotides for use in treating hereditary sensory neuropathy type I, and pharmaceutical compositions comprising such oligonucleotides.

BACKGROUND

Hereditary sensory neuropathy type I (HSN1) is the most common form of HSN, a peripheral neuropathy affecting the sensory neurons. HSN1 patients present with loss of sensation that can lead to severe consequences, such as skin ulcerations, recurrent injuries and distal amputations.

HSN1 is caused by dominant mutations in the serine palmitoyltransferase long chain subunit 1 gene (SPTLC1). It has been found that haploinsufficiency of SPLTC1 is not pathogenic as demonstrated by non-symptomatic transgenic heterozygous Sptlc1 knockout mice. SPTLC1 encodes a subunit of the enzyme serine palmitoyltransferase (SPT) that is involved in sphingolipid biosynthesis in cells. In HSN1 the substrate preference of SPT is changed from serine to alanine, leading to the formation of toxic sphingolipids. All the UK HSN1 population share the same missense variation (c.399T>G/p.C133W) in SPTLC1. There is no cure available currently.

SUMMARY OF THE INVENTION

The present inventors have developed a new therapeutic strategy for the treatment of HSN1. They have identified antisense oligonucleotides (AONs) and small interference RNAs (siRNAs) that are able to supress an allele carrying a dominant mutation causing HSN1 with significant selectivity and efficiency, without influencing the transcription of the wild type allele. A number of chemical modifications with different AON designs have been tested, including but not limited to phosphorothioated DNA, 2'-O-Methyl RNA, Locked nucleic acid (LNA) RNA and 2'-deoxy-2'-fluoro-beta-D-arabinonucleic acid (2'-FANA) RNA.

Hence, the invention provides an oligonucleotide that supresses the expression of an allele carrying a dominant mutation that causes hereditary sensory neuropathy type I (HSN1), wherein the suppression takes place through hybridisation of said oligonucleotide to the DNA of said allele or to an RNA transcript of said allele, and which either does not suppress the expression of a wild-type allele not containing the dominant mutation or suppresses the expression of said wild-type allele to a lesser extent than it suppresses the expression of the dominant mutant allele.

The invention also provides a pharmaceutical composition comprising the oligonucleotide of the invention, together with a pharmaceutically acceptable carrier or excipient.

The invention also provides an oligonucleotide of the invention for use in a method of treating HSN1, the method comprising administering said oligonucleotide to a subject, wherein the oligonucleotide supresses expression of an allele carrying a dominant mutation that causes said HSN1, wherein the suppression takes place through hybridisation of said oligonucleotide to the DNA of said allele or to an RNA transcript of said allele, and which either does not suppress the expression of a wild-type allele not containing the dominant mutation or suppresses the expression of said wild-type allele to a lesser extent than it suppresses the expression of the dominant mutant allele.

The invention also provides the oligonucleotide of the invention in the manufacture of a medicament for treating HSN1.

The invention also provides a method of treating HSN1 comprising administering an effective amount of the oligonucleotide of the invention to a subject suffering from HSN1.

DETAILED DESCRIPTION

Oligonucleotides

Figure 1:
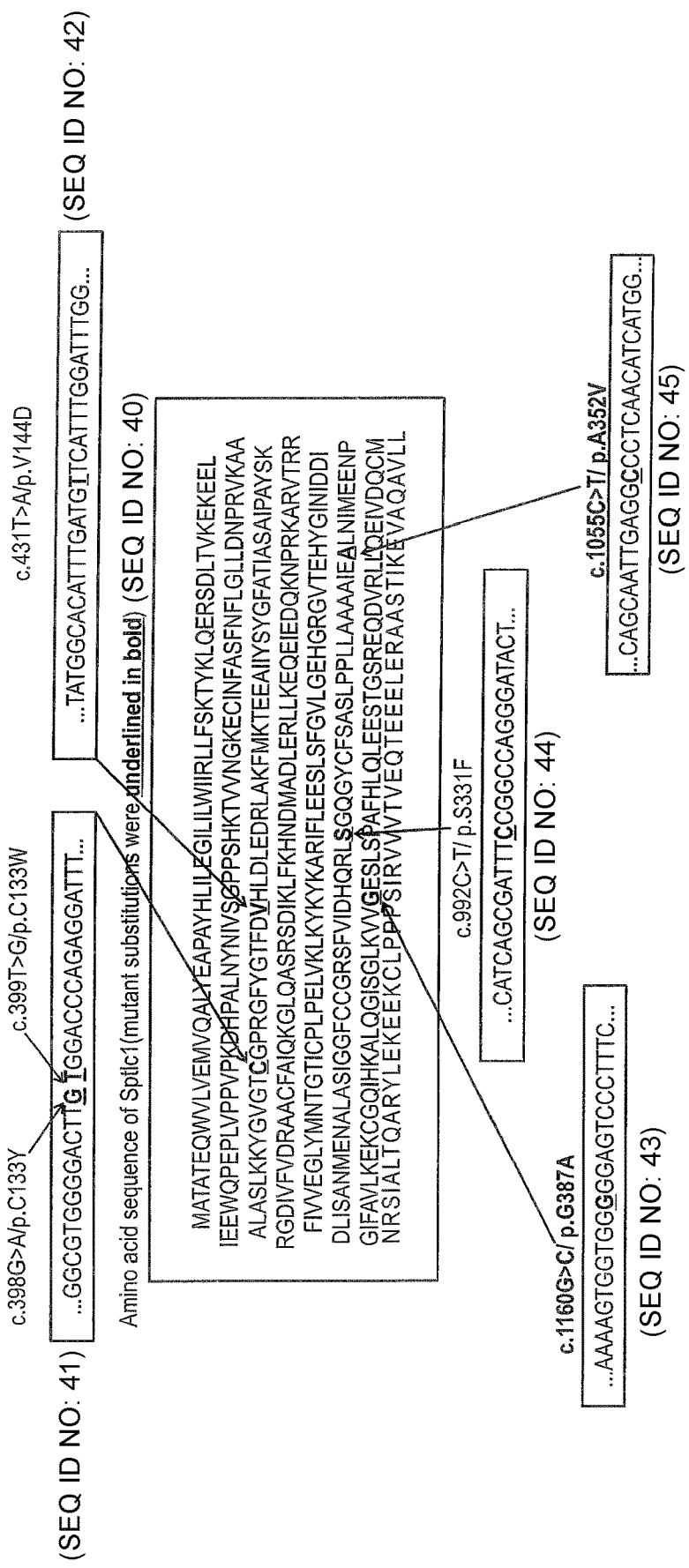
FIG. 1: The location of 6 mutations identified in SPTLC1 gene. The amino acid sequence of the serine palmitoyltransferase coded by the SPTLC1 gene is presented. The mutant amino acids are in bold and underlined. The corresponding nucleic acid changes and related mutations are presented and indicated with arrows.

The present invention provides oligonucleotides that are able to supress an allele carrying a dominant mutation causing HSN1 with significant selectivity and efficiency. This is achieved with no or less than 5%, 10%, 15%, 20%, 25%, 30%, 35%, 40%, 45%, 50% suppression of the expression of the wild-type allele. An oligonucleotide sequence of the invention may be capable of inhibiting the effect of a mutant SPTLC1 gene. Hence, by employing the invention, the mutant gene can be supressed and hence treat HSN1.

In the context of this invention, the term "oligonucleotide" refers to an oligomer of nucleotide or nucleoside monomers consisting of naturally-occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides, which are oligomers of DNA or RNA molecules. A deoxyribooligonucleotide consists of a 5-carbon sugar (deoxyribose) which is joined covalently to phosphate at the 5' and 3' carbons of the sugar to form an alternating, unbranched polymer. A ribooligonucleotide consists of a similar repeating structure where the 5-carbon sugar is ribose.

The oligonucleotides described herein can be single-stranded DNA or RNA, double-stranded DNA or RNA, DNA-RNA hybrids, or chimeric DNA-RNA structures. Examples of double-stranded RNA include, e.g., siRNA, short hairpin RNA (shRNA) and other RNAi agents such as pre-miRNA. Single-stranded oligonucleotides include, e.g., antisense oligonucleotides, ribozymes, mature miRNA, and triplex-forming oligonucleotides.

Using known techniques and based on a knowledge of the sequence of the allele carrying a dominant mutation, double-stranded RNA (dsRNA) molecules can be designed to suppress the allele by sequence homology-based targeting of its RNA transcript. Such dsRNAs will typically be siRNAs, usually in a stem-loop ("hairpin") configuration, or micro-RNAs (miRNAs). The sequence of such dsRNAs will comprise a portion that corresponds with that of a portion of the mRNA transcript. This portion will usually be 100% complementary to the target portion within the allele comprising the dominant mutation but lower levels of complementarity (e.g. 60% or more, 65% or more, 70% or more, 75% or more, 80% or more, 85% or more, 90% or more, or 95% or more) may also be used.

Using known techniques and based on a knowledge of the sequence of the allele carrying a dominant mutation, single-stranded antisense oligonucleotides (AONs) can be designed to suppress the allele by sequence homology-based targeting of its RNA transcript. The sequence of such AONs will comprise a portion that corresponds with that of a portion of the mRNA transcript. This portion will usually be 100% complementary to the target portion within the allele comprising the dominant mutation but lower levels of complementarity (e.g. 60% or more, 65% or more, 70% or more, 75% or more, 80% or more, 85% or more, 90% or more or 95% or more) may also be used. In one embodiment, the oligonucleotide is an antisense oligonucleotide (AON). The AON acts by binding to pre-mRNA or mRNA via Watson-Crick base pairing and induces gene suppression by different mechanisms such as through RNase H-mediated mRNA degradation. The AON has a base sequence that is complementary to the mRNA of the allele carrying the dominant mutation. They are prone to rapid degradation by intracellular endonucleases and exonucleases.

The AONs of the invention can be gapmers or altimers. A gapmer is a chimeric AON that contains a central block of DNA molecules and is flanked by blocks of 2'-O modified ribooligonucleotides or other artificially modified ribooligonucleotide monomers that protect the internal block from nuclease degradation. The oligonucleotides contain DNA bases, wherein some or all of the DNA bases have a phosphorothioated backbone. For example, none, 5 or more, 10 or more, 15 or more, 20 or more, 25 or more, or all of the DNA bases have a phosphorothioated backbone. DNA that contain phosphorothioated backbones provide an increased resistance to nucleases compared to unmodified DNA.

In a preferred embodiment, the AON comprises modifications to help enhance the properties of the oligonucleotide. Hence, the oligonucleotide of the invention may be modified by the substitution of at least one nucleotide with at least one modified nucleotide, ideally so that the in vivo and in vitro stability of the oligonucleotide is enhanced as compared to a corresponding unmodified oligonucleotide. The modified nucleotide may, for instance, be a sugar-modified nucleotide or a nucleobase-modified nucleotide. In some instances, two, three, four, five, six or seven modified nucleotides may be included, or at least that number, in others eight, nine, ten, eleven or twelve such modifications, or at least that number, may be included, in other cases, fifteen, twenty, twenty-one, twenty-two, twenty three, twenty-four, twenty-five or at least such numbers may be modified. In still others all of the nucleotides may be modified, or all but one, two, three, four or five nucleotides.

In some instances, the modified nucleotide is a 2'-deoxy ribonucleotide. In certain instances, the 2'-deoxy ribonucleotide is 2'-deoxy guanosine or 2'-deoxy adenosine. In other instances, the modified nucleotide is a 2'-O-methylguanosine, 2'-O-methyl (e.g., 2'-O-methylcytidine, 2'-O-methylpseudouridine, 2'-O-methyluridine, 2'-O-methyladenosine, 2'-O-methyl) ribonucleotide. In some cases, the modified nucleotide is selected from a 2'-amino, 2'-thio and 2'-fluoro modified ribonucleotide. In a further instances, the modified nucleotide is selected from the group consisting of 2'-fluoro-cytidine, 2'-fluoro-uridine, 2'-fluoro-guanosine, 2'-fluoro-adenosine, 2'-amino-cytidine, 2'-amino-uridine, 2'-amino-adenosine, 2'-amino-guanosine, 2'-amino-butyryl-pyrene-uridine and 2'-amino-adenosine. In an additional instances, the modified nucleotide is selected from 5-iodo-uridine, ribo-thymidine, 5-bromo-uridine, 2-aminopurine, 5-methylcytidine, 5-fluoro-cytidine, and 5-fluoro-uridine, 2,6-diaminopurine, 4-thio-uridine, and 5-amino-allyl-uridine. In some instances, the modified nucleotide includes: derivatization of the 5 position, for instance being selected from 5-(2-amino) propyl uridine, 5-bromo uridine, 5-propyne uridine, 5-propenyl uridine; derivatization of the 6 position, for instance 6-(2-amino)propyl uridine; derivatization of the 8-position for adenosine and/or guanosines, for instance 8-bromo guanosine, 8-chloro guanosine, or 8-fluoroguanosine, Nucleotide analogs which may be employed include deaza nucleotides, e.g., 7-deaza-adenosine; O- and N-modified (for instance alkylated, such as N6-methyl adenosine) nucleotides; and other heterocyclically modified nucleotide analogs. Examples of modifications to the sugar portion of the nucleotides which may be employed include the 2' OH-group being replaced by a group selected from H, OR, R, F, Cl, Br, I, SH, SR, NH2, NHR, NR2, COOR, or OR, wherein R is substituted or unsubstituted C1-C6 alkyl, alkenyl, alkynyl, aryl and so on. The phosphate group of the nucleotide may also be modified, such as by substituting one or more of the oxygens of the phosphate group with sulphur (for instance by employing phosphorothioates). Modifications may decrease the rate of hydrolysis of polynucleotides comprising the modified bases, for example by inhibiting degradation by exonucleases. In one preferred instance, the oligonucleotide is resistant to ribonucleases. Oligonucleotides which may be employed include those with modifications to promote such resistance, for instance an oligonucleotide of the invention may have preferably been modified with a 2'-O-methyl group (e.g., 2'-O-methylcytidine, 2'-O-methylpseudouridine, 2'-O-methylguanosine, 2'-O-methyluridine, 2'-O-methyladenosine, 2'-O-methyl) and additionally comprise a phosphorothioate backbone.

In some instances, oligonucleotides comprise oligonucleotides that contain phosphorothioate and 2'-O-methyl (e.g., 2'-O-methylcytidine, 2'-O-methylpseudouridine, 2'-O-methylguanosine, 2'-O-methyluridine, 2'-O-methyladenosine, 2'-O-methyl) modification. Other forms of oligonucleotide modifications may be employed, for example, locked nucleic acids (oligonucleotides comprising at least one 2'-C, 4'-C-oxy-methylene-linked bicyclic ribonucleotide monomer). In some instances the modified nucleotide employed may be 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluraci 1,5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In some instances, the modified oligonucleotide may include modifications to the phosphate backbone such as methyl phosphonates, methyl phosphonothioates, phosphoromorpholidates, phosphoropiperazidates and phosphoramidates. In one example, every other one of the internucleotide bridging phosphate residues may be modified as described. In another non-limiting example, such oligonucleotides are oligonucleotides wherein at least one, or all, of the nucleotides contain a 2' loweralkyl moiety (e.g., C1-C4, linear or branched, saturated or unsaturated alkyl, such as methyl, ethyl, ethenyl, propyl, 1-propenyl, 2-propenyl, and isopropyl).

In one embodiment, the oligonucleotide is a small interfering RNA (siRNA). An siRNA acts by activating the RNAi-induced suppression complex. The siRNA molecules can be unmodified or modified and are capable of supressing gene expression. They are typically about 15 to 60 nucleotides in length. In some embodiments, the modified siRNA contains at least one 2'O-Me purine or pyrimidine nucleotide such as a 2'O-Me-guanosine, 2'O-Me-uridine, 2'O-Me-adenosine, and/or 2'O-Me-cytosine nucleotide.—The modified nucleotides can be present in one strand (i.e., sense or antisense) or both strands of the siRNA. The siRNA sequences may have overhangs or blunt ends.

The modified siRNA may comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides.

Suitable siRNA sequences can be identified using any means known in the art. Typically, the methods described in Elbashir et al., *Nature*, 411:494-498 (2001) and Elbashir et al., *EMBO J.*, 20:6877-6888 (2001) are combined with rational design rules set forth in Reynolds et al., *Nature Biotech.*, 22(3):326-330 (2004).

Preferably, siRNA are chemically synthesized. The oligonucleotides that comprise the siRNA molecules of the invention can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). The synthesis of oligonucleotides makes use of common nucleic acid protecting and coupling groups, such as dimethoxytrityl at the 5'-end and phosphoramidites at the 3'-end. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

In one embodiment, the oligonucleotide is a guide RNA comprising a guide RNA sequence and a tracr RNA. The guide RNA sequence is capable of hybridizing to a target sequence in the DNA of an allele. The tracr RNA is coupled to the guide RNA sequence. The guide RNA hybridises to the site of the allele carrying a dominant mutation and targets a CRISPR-Cas enzyme to said site. In some embodiments, the guide sequence is between 10-30, or between 15-25, or between 15-20 nucleotides in length. Preferably the CRISPR-Cas enzyme is a Type II CRISPR enzyme, for example Cas-9. The enzyme complexes with the guide RNA. In one embodiment, the complex is targeted to the DNA sequence of the dominant mutant allele and will bind by hybridization. In one embodiment, the enzyme is active and acts as an endonuclease to cleave the DNA either via activation of the non-homologous end-joining or homologous DNA repair pathway, resulting in a blunt end cut or a nick. A repair template sequence can be supplied and be introduced into the allele by homologous recombination, thereby replacing the sequence that it targeted, such as a mutation in the DNA of an allele. In another embodiment, the enzyme is targeted to the DNA of the dominant mutant allele but the enzyme comprises one or more mutations that reduce or eliminate its endonuclease activity such that it does not edit the mutant allele but does prevent or reduce its transcription. In another embodiment, the enzyme can be engineered such that it is fused to a transcriptional repressor to reduce or disable its endonuclease function. The enzyme will be able to bind the guide RNA and be targeted to the DNA sequence, but no cleavage of the DNA takes place. The mutant allele may be suppressed, for example, by the shutting down of the promoter or blockage of RNA polymerase. In another embodiment, the transcription repressor may be bound to the tracr sequence. Functional domains can be attached to the tracr sequence by incorporating protein-binding RNA aptamer sequences, as described in Konermann et al (Genome-scale transcriptional activation by an engineered CRISPR-Cas9 complex, Nature, Vol 000, 2014). The transcription repressor-tracr sequence complex may be used to target other moieties to a precise gene location as desired.

An oligonucleotide of the invention may be conjugated with a peptide or receptor. To assist with delivery of the oligonucleotide, the peptide may for example be a cell penetrating peptide. This technique is described in, for example, WO2009/147368, WO2013/030569, WO2012/150960 and WO2004/097017.

The oligonucleotides of the invention are complementary to a region of the RNA transcript from the SPTLC1 gene. In one instance, the oligonucleotide will be complementary to 10, 11, 12, 13, 14, 15, 16, 17, 18, 19, 20, 21, 22, 23, 24, 25, 26, 27, 28, 29, or 30 nucleotides of that sequence, preferably complementary to 13-25 or 16-21 nucleotides of that sequence.

In one instance, the oligonucleotide is at least 10, 11, 12, 13, 14, 15, 16, 17, 18, 19, 20, 21, 22, 23, 24, 25, 26 or 27 nucleotides in length, preferably at least 23, 24, 25 or 26 nucleotides in length, for example 13-25 or 16-21 nucleotides in length. It may be that the region of the oligonucleotide capable of hybridisation to is that length, or at least that length, but there are also additional nucleotides at the 5' and/or 3' ends of the oligonucleotide, though in other instances the overall length of the oligonucleotide is that number of nucleotides.

In general, oligonucleotide sequences which are perfectly complementary to a portion of the target RNA may preferably be employed. In some instances though sequence variations that might be expected due to genetic mutation, strain polymorphism, or evolutionary divergence may be present. For example, oligonucleotide sequences with insertions, deletions, and single point mutations relative to the target sequence may also be effective for inhibition. Greater than 70% sequence identity (or complementarity), e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the oligonucleotide sequence and the target RNA, e.g., target pre-mRNA, is preferred.

Sequence identity, including determination of sequence complementarity for nucleic acid sequences, may be determined by sequence comparison and alignment algorithms known in the field. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions*100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Some preferred AONs of the invention include

[CUGGG]TCCCCAA[GUCCC]; (SEQ ID NO: 1)

<UGGGU>CCCCA<AGUCC>; (SEQ ID NO: 2)

<UGG>GTC<CCC>AAG<UCC>; (SEQ ID NO: 3)

wherein [ ] denotes a 2'O-Me RNA base, and < > denotes a 2'FANA RNA base.

In some instances, the total length of the oligonucleotide may be up to 100, 90, 80, 70, 60, 50, 40, or 30 nucleotides. In others, the total length may be 29, 28, 27, 26, 25, 24, 23, 22, 21, 20, 19, 18, 17, 16, 15, 14, 13, 12, 11 or 10 nucleotides, particularly 14-25 nucleotides.

The oligonucleotide of the invention may also hybridise to a site within the dominant mutant allele that is not itself the site of the dominant mutation. This site may be a site with a polymorphism, such as a Single Nucleotide Polymorphism (SNP), microsatellite polymorphism, insertion polymorphism and deletion polymorphism. Preferably the polymorphism is a SNP. Such polymorphisms may be identified by genotyping the subject and sequencing the mutant allele present in their genome, or they may be known or suspected to be present a priori. Typically, the nucleotide present at the same position on both the dominant mutant allele and wild-type allele will be determined. Targeting an oligonucleotide of the invention to such a mutation in the dominant mutant allele will suppress the allele and effect treatment of HSN1, even if the mutation targeted is non-causative of the disease. Further, both the causative mutation and one or more non-causative ones can be targeted with different oligonucleotides.

Suppression of the expression of an allele carrying a dominant mutation can be measured by any suitable technique known in the art. For example, reverse transcription, Sanger sequencing and quantitative real-time PCR is a frequently used technique. The oligonucleotides of the invention can suppress the expression of the allele by any amount, preferably up to 95%, 90%, 85%, 80%, 75%, 70%, 65%, 60%, 55%, 50%, 45%, 40%, 30%, 20% or 10%.

HSN1 Mutations

There are six reported mutations in the SPTLC1 gene. These are c.399T>G/p.C133W, c.398G>A/p.C133Y, c.431T>A/p.V144D, c.992C>T/p.S331F, c.1055C>T/p.A352V, c.1160G>C/p.G387A. c.1160G>C/p.G387A is not a pathogenic variant, whereas the other five mutations are known to be pathogenic (i.e. causing HSN1). Any of these mutations can be targeted according to the invention.

Methods of Therapy and Medical Uses

The present invention relates to a method of treating HSN1. The method comprises administering to a subject the oligonucleotide or pharmaceutical composition of the invention and thereby treating HSN1. The present invention also relates to the oligonucleotide or pharmaceutical composition of the invention for use in a method of treating HSN1, the method comprising administering the oligonucleotide or pharmaceutical composition to a subject, wherein the oligonucleotide or pharmaceutical composition supresses an allele carrying a dominant mutation causing HSN1. The present invention also relates to the use of the oligonucleotide or pharmaceutical composition of the invention in the manufacture of a medicament for treating HSN1.

The method may be for treating the disease or disorder. In the case of treating, the patient typically has the disease or disorder, i.e. has been diagnosed as having the disease or disorder, or is suspected as having the disease or disorder, i.e. shows the symptoms of the disease or disorder. As used herein, the term "treating" includes any of following: the prevention of the disease or disorder or of one or more symptoms associated with the disease or disorder; a reduction or prevention of the development or progression of the disease or disorder or symptoms; and the reduction or elimination of an existing disease or disorder or symptoms.

Specific routes, dosages and methods of administration of the therapeutic agents described herein may be routinely determined by the medical practitioner. These are discussed in more detail below.

Means of Delivery

Oligonucleotide sequences may be introduced into cells using any suitable method. For instance, transfection, electroporation, fusion, liposomes, colloidal polymeric particles and viral and non-viral vectors as well as other means known in the art may be used to deliver the oligonucleotide sequences to cells. In some instances, the oligonucleotide may be delivered using methods involving liposome-mediated uptake. Lipofectins and cytofectins are lipid-based positive ions that bind to negatively charged nucleic acid and form a complex that can ferry the nucleic acid across a cell membrane and may be employed. In one instance a lipofectin is used in the delivery of the oligonucleotide of the invention, particularly Lipofectamin$^{2000}$. In some instances, no transfection reagents may be required and oligonucleotide may be uptaken by cells directly via gymnosis.

Delivery may be direct to the patient, or for instance to cells or tissues, for instance with the cells or tissues subsequently being reintroduced. Oligonucleotide sequences may be directly introduced into the cell or introduced extracellularly into a cavity, interstitial space, into the circulation of an organism, introduced orally, or may be introduced by bathing a cell or organism in a solution containing the RNA using methods for introducing nucleic acid into cells in vivo. The oligonucleotides of the invention may be delivered by any suitable route of administration. In some instances, administration may be systemic, in others it may be localised. For instance, the oligonucleotides may be administered by direct injection at a tissue site or infusion into a body fluid. Vascular or extravascular circulation, the blood or lymph system, and the cerebrospinal fluid are examples of locations where the RNA may be introduced.

The oligonucleotide reagents of the invention may be, for instance, delivered to the nervous system of a subject by any suitable method. For example, injection and in particular intravenous injection of the oligonucleotide reagents of the invention can be used for delivery to peripheral neurons via diffusive and/or active means. Alternatively, the oligonucleotides can be modified to promote crossing of the blood-brain-barrier (BBB) to achieve delivery of said reagents to neuronal cells of the central nervous system (CNS). In certain instances, the oligonucleotides can be delivered by transdermal methods. The oligonucleotide may also be delivered via an implantable device.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle can be used to achieve efficient introduction into a cell and transcription of RNA encoded by the expression construct. Other methods known in the art for introducing nucleic acids to cells may be used, such as lipid-mediated carrier transport, chemical-mediated transport, such as calcium phosphate, and the like. RNA may be introduced along with components that perform one or more of the following activities: enhance RNA uptake by the cell, inhibit annealing of single strands, stabilize the single strands, or other-wise increase inhibition of the target gene.

The oligonucleotides may be modified so that they target specific cells, for instance by binding to receptors found on a particular cell type. The oligonucleotides may be delivered to cells using a vector.

Pharmaceutical Compositions

The present invention also provides a pharmaceutical composition comprising an oligonucleotide of the invention. The composition will also typically comprise a pharmaceutically acceptable carrier or excipient. The composition may be formulated to help it be compatible with its intended route of administration.

Examples of routes of administration which may be employed in the invention, and which in some cases the composition may be formulated to aid compatibility with include parenteral, e.g., intravenous, intradermal, subcutaneous, intraperitoneal, intramuscular, oral (e.g., inhalation), transdermal (topical), transmucosal, and direct CNS delivery may be employed, for instance, intracerebral ventribular or intrathecal administration may be employed. The oligonucleotides of the invention may be, for instance, delivered by such routes.

Pharmaceutical compositions of the invention, including in particular solutions or suspensions used for parenteral, intradermal, or subcutaneous application, may, for example, include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. Possible excipients may in some instances be selected from water, salt solutions, alcohol, polyethylene glycols, gelatin, lactose, amylase, magnesium stearate, talc, silicic acid, viscous paraffin, hydroxymethylcellulose and polyvinylpyrrolidone. The pH of the composition may be adjusted with acids or bases, such as hydrochloric acid or sodium hydroxide. The composition, for instance a composition for parenteral preparation, may be enclosed in ampoules, disposable syringes or multiple dose vials made of glass or plastic. In a preferred instance, a composition of the invention has a physiological pH.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers may include physiological saline, bacteriostatic water, Cremophor EL(™) (BASF, Parsippany, N.J.) or phosphate buffered saline (PBS). The compositions will typically be sterile, particularly those for intravenous administration.

The carrier present in a composition of the invention may, for instance, be a solvent or dispersion medium containing, for example, water, ethanol, polyol (for example, glycerol, propylene glycol, or liquid polyetheylene glycol) as well as suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions may be prepared, for instance, by incorporating the active compound in the required amount in an appropriate solvent with one or a combination of ingredients enumerated above, as required, followed by filtered sterilization. In the case of sterile powders for the preparation of sterile injectable solutions, preferred methods of preparation include vacuum drying and freeze-drying which yields a powder of the active ingredient plus any additional desired ingredient from a previously sterile-filtered solution thereof.

Pharmaceutical compositions comprising oligonucleotides of the invention encompass any pharmaceutically acceptable salts, esters, or salts of such esters of the oligonucleotide. In certain instances, a composition of the invention may include more than one oligonucleotide of the invention. Accordingly, for example, the disclosure is also drawn to pharmaceutically acceptable salts, prodrugs, pharmaceutically acceptable salts of such prodrugs, and other bioequivalents may also be employed. Suitable pharmaceutically acceptable salts include, but are not limited to, sodium and potassium salts. A prodrug may, for instance, include the incorporation of additional nucleosides at one or both ends of an oligomeric compound which are cleaved by endogenous nucleases within the body, to form the active oligonucleotide.

Administration may be, for instance, by inhalation. Systemic administration may be, for instance, by transmucosal or transdermal means. Transmucosal administration can be accomplished through the use of nasal sprays or suppositories. For transdermal administration, the oligonucleotides may be, for instance, formulated into ointments, salves, gels, or creams. The oligonucleotides may be, for instance, prepared in the form of suppositories or retention enemas. In some instances, the oligonucleotides may be formulated with carriers that protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid.

In one instance, the pharmaceutical compositions may be formulated in unit dosage forms. In some cases the compositions may be formulated in ampoules. The pharmaceutical compositions may be included in a container, pack, or dispenser together with instructions for administration. A kit comprising an oligonucleotide of the invention and optionally instructions for administration to treat HSN1 is also described, preferably such a kit has the oligonucleotide provided in the form of a pharmaceutical composition of the invention. The kit may also include means for administering the oligonucleotide or composition, for instance a syringe or other appropriate delivery device. The kit may comprise any of the means of delivery discussed herein. In one instance, the kit also comprises lipofectin and in particular the oligonucleotide formulated with lipofectin.

The dosage of the oligonucleotide administered will depend upon the particular method being carried out, and when it is being administered to a subject, the nature of disease, the condition of the subject, the particular formulation, and the route of administration. Examples of intracellular concentrations of the oligonucleotide include those in the range from about 0.005 to 50 or more preferably 0.02 to 5 µM. For administration to a subject such as a human, a daily dosage ranging from about 0.001 to 50 mg/kg, preferably 0.01 to 10 mg/kg, and more preferably from 0.1 to 5 mg/kg may be employed. The skilled person and particularly an appropriate physician will be able to identify an appropriate dosage, for instance taking factors such as age, sex, weight and so on into account.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the oligonucleotide in the patient and the duration of treatment desired.

Oligonucleotides of the invention may be co-administered with one or other more other therapeutic agents.

The following Examples, which do not limit the scope of the invention, further illustrate the principles of the present invention.

EXAMPLES

Materials and Methods

Antisense Oligonucleotides (AONs) and siRNAs

The 2'-O-Methyl (2'-O-Me) RNA, phosphorothioated DNA and locked nucleic acid (LNA) RNA AONs were commercially synthesised by Eurogentec Ltd (Belgium). Custom siRNAs were synthesized by Eurofins Scientific Ltd (Germany). The 2'-deoxy-2'-fluorobeta-D-arabinonucleic acid (2'FANA) RNA oligonucleotides were manufactured by the AUM LifeTech Ltd (USA). The list of 17 AONs and 7 siRNAs screened in this study is shown in Table 1.

Transfection of HSN1 Fibroblasts

A skin fibroblast cell line established from a HSN1 patient carrying the c.399T>G mutation in SPTLC1 was used as a cellular model to test the allele-specific gene suppression.

The cells were grown in Dulbecco's Modified Eagle Medium+GlutaMAX (4.5 g/L D-Glucose, Pyruvate) (Gibco) supplemented with 10% Fetal Bovine Serum (Gibco) and 1% L-Glutamine (Gibco) at 37° C. in 5% $CO_2$. Cells were plated into 6-well plates at $1 \times 10^5$ cells/well, which gave >80% confluence when transfected the next day. AONs were complexed with Lipofectamine 2000 (Invitrogen) in Opti-MEM (Invitrogen) according to the manufacturer's instructions, and added to the cells. Cells were harvested 24 hours after transfection for RNA extraction. For siRNAs, Dharmafect (GE Healthcare) was used as transfection reagent following the manufacturer's instructions.

RNA Extraction and cDNA Synthesis

Total RNA was extracted from cells using RNeasy® Mini Kit (Qiagen) according to the manufacturer's instructions. Complementary DNA was synthesised from 500 ng RNA using the SuperScript® III First-Strand Synthesis System (Invitrogen). Complementary DNA (cDNA) was stored at −20° C.

Reverse Transcription PCR and Sanger Sequencing

Polymerase chain reaction for samples to be sequenced was carried out using pfx polymerase (Invitrogen). Primers (F: 5'-AACATCGTTTCAGGCCCTC-3' (SEQ ID NO: 4), R: 5'-GCAAAGCAGGCAGCTCTATC-3' 3' (SEQ ID NO: 5)) were used to amplify a 335 bp product in the SPTLC1 gene (ENSG00000090054) in which the c.399T>G variation is located. PCR conditions included 94° C. for 3 min for template denaturing, followed by 30 PCR cycles of 94° C. for 30 seconds, 55° C. for 30 seconds and 72° C. for 30 seconds and final extension for 10 minutes at 72° C. All PCR products were run on 2% agarose gels and visualized under UV light. The PCR product was purified using PCR purification kit® (Qiagen) according to the manufacturer's instructions. The purified PCR products were examined using genomic sequencing by SourceBioscience Ltd (Cambridge, UK). The sequencing data was analysed using Sequencher 4.10.1 software.

Quantitative Real-Time PCR

Quantitative real-time PCR (qPCR) was carried out in StepOnePLUS thermal cycler using Takyon™ Rox SYBR® MasterMix dTTP Blue (Eurogentec). Allele-specific primers were used to amplify a 130 bp wild-type SPTLC1 allele (F: 5'-TATGGCGTGGGGACTTGT-3' (SEQ ID NO: 6), R: 5'-ACTGGCTATGGTGGCAAATC-3ISEQ ID NO: 7)) and a 130 bp mutant SPTLC1 allele (F: 5'-TATGGCGTGGGGACTTGG-3' (SEQ ID NO: 8), R: 5'-ACTGGCTATGGTGGCAAATC-3' (SEQ ID NO: 9)). A 117 bp Glyceraldehyde 3-phosphate dehydrogenase (GAPDH) was amplified as an internal control (F: 5'-TTGAGGTCAATGAAGGGGTC-3' SEQ ID NO: 10), R: 5'-GAAGGTGAAGGTCGGAGTCA-3' (SEQ ID NO: 11)). The results were quantified using the relative standard curve method and analysed by the StepOne software. The expression of wild type and mutant allele of the treated samples were normalized taking the expression of the scrambled control AON treated sample as 1.0. Scrambled control AONs were designed with at least four mismatches in the sequence to interrupt the complete complementarity to the target sequence. Scrambled AON sequences have been blasted such that they do not bind to any known genes. Scrambled AONs share the same backbone as the tested AONs.

Results

Design of AONs and siRNAs for Allele-Specific Gene Suppression

AONs act by binding to pre-mRNA or mRNA via Watson-Crick base pairing and are able to induce gene suppression by different mechanisms. Recruitment and activation of RNase H, an endogenous endonuclease which recognises DNA-RNA hybrid and cleaves the RNA strand, has been widely used in AON-mediated gene suppression. Considering the founder effect of mutation c.399T>G in UK population, we have designed AONs to specifically anneal to the locus of this mutation. Different parameters have been considered in the AONs' design, including the sequence length and chemical modification of the RNA backbone, with aims to improve the suppression efficiency and specificity. A list of 17 AONs designed in this study is shown in Table 1 and FIG. 2.

The AONs are designed as chimeric oligonucleotide sequences and are composed of both DNA and RNA bases. All the DNA bases in our AONs have a phosphorothioated backbone (PS). Three different chemical modifications of the RNA backbone have been evaluated in our study. These include 2'-Me RNA modification, LNA RNA sugar structure modification, and 2'FANA RNA modification.

AONs are usually designed to be 14-25 nucleotides long. The length of the AON may significantly affect its binding affinity to a target sequence. Usually, the longer the sequence, the higher the binding affinity. However, a long AON sequence on the other hand can affect the specificity for allele discrimination. Therefore, in this study we tested different lengths of AONs in order to identify the optimal sequence with the maximum potential in gene-suppression and allele-specificity.

Screening the Allele-Specific Suppression Ability of AONs and siRNAs

Figure 3:
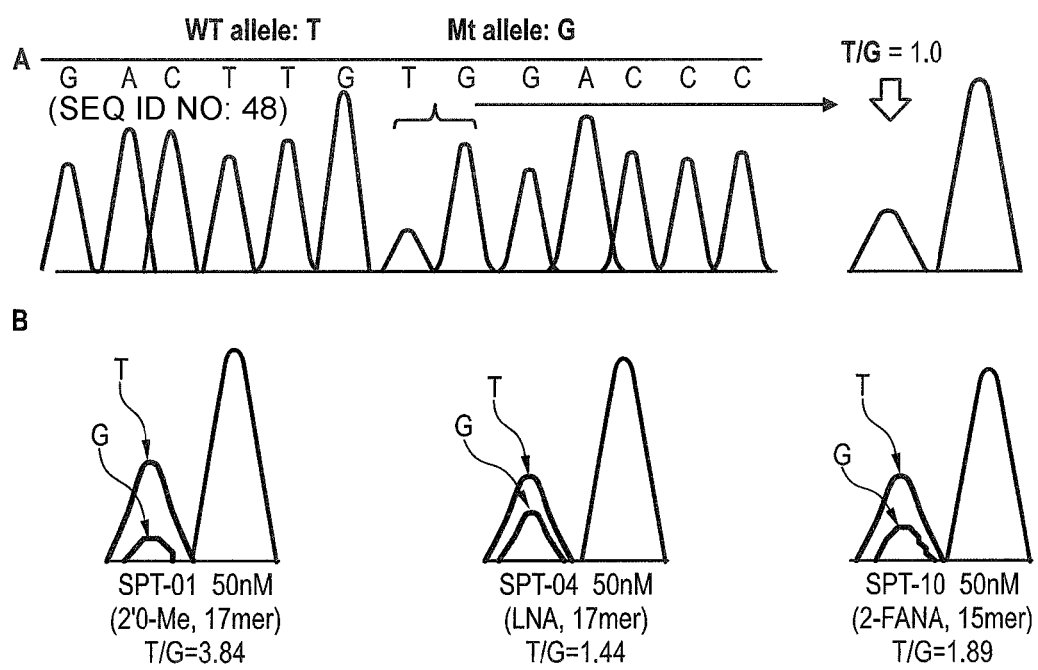
FIG. 3: Chromatograms generated from the analysis of the heterozygous c.399 T>G mutation in PCR products amplified from the patient's fibroblasts that were treated with the different AONs. The ratio of T (wild type allele) to G (mutant allele) was set as 1.0 in the scramble treated fibroblasts. The expression of the wild type and mutant alleles was measured by allele-specific real-time PCR. (A) In a control sample which was treated with scrambled AON. (B) In samples treated with AONs with different RNA backbones.

Chromatograms of the heterozygous c.399 T>G mutation in the SPTLC1 gene were generated based on DNA sequencing results of the PCR products amplified from the fibroblasts treated with AONs. The 17-mer 2'-O-Me based AON (SPT-01) showed the highest efficiency in suppression of the mutant G-allele and retaining the expression of the wild type T-allele (FIG. 3).

Figure 4:
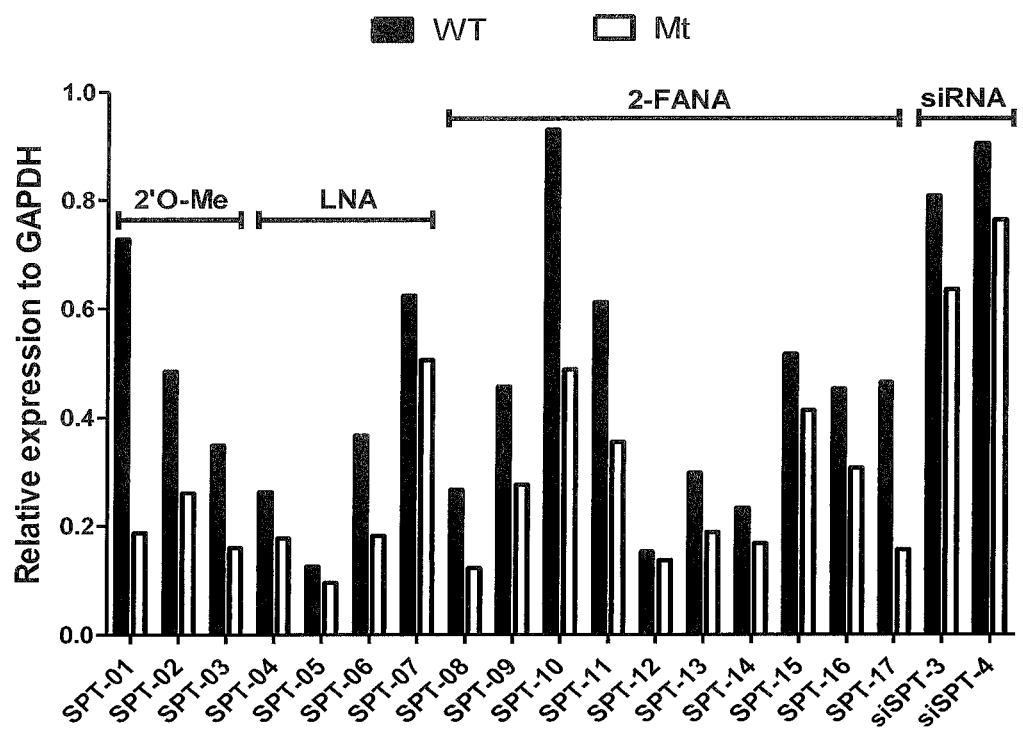
FIG. 4: Screening of AONs in allele-specific suppression by quantitative real-time PCR.
Figure 5:
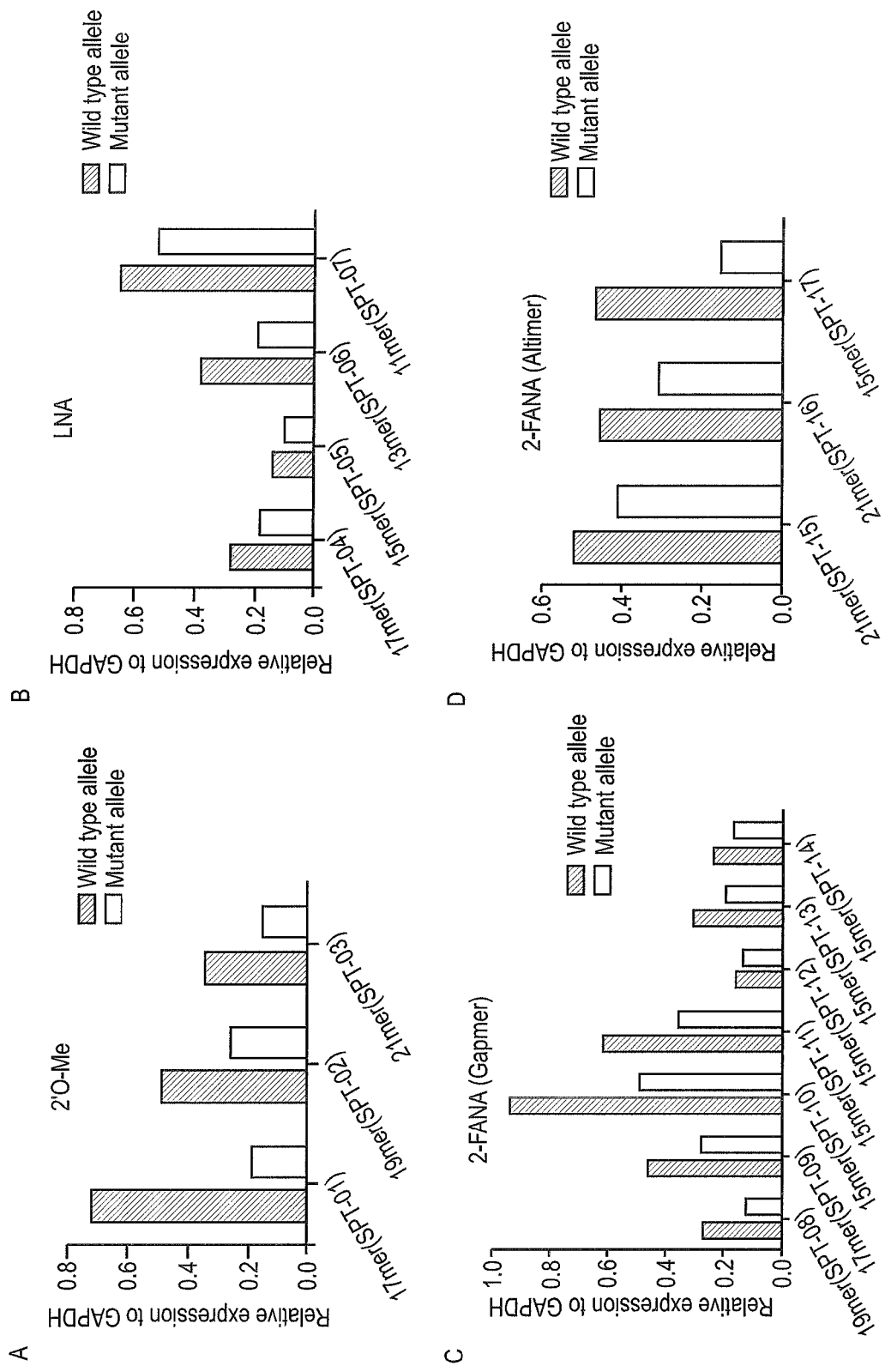
FIG. 5: Expression of the wild type and mutant alleles in the patient's fibroblasts treated with AONs with (A) 2'O-Me RNA modification, (B) LNA backbone modification, (C) 2-FANA backbone modification in Gapmer and (D) Altimer design.

We have screened 17 AONs and some siRNAs by quantifying the expression of both the wild type and the mutant alleles in fibroblasts treated with the different AONs, using quantitative allele-specific real-time PCR (FIG. 4). For AONs with a 2'-O-Me RNA backbone, SPT-01 (17-mer) showed an approximate 80% suppression of the mutant G-allele and the reservation of over 70% of the wild type T-allele (FIG. 5A). For AONs with an LNA backbone, all AONs showed dramatic suppression of both T and G-allele (FIG. 5B). For AONs with a 2'-FANA RNA backbone, both the 15-mer AON Gapmer (SPT-10) and Altimer (SPT-17) gave efficient allele-specific suppression (FIGS. 5C & D).

Figure 6:
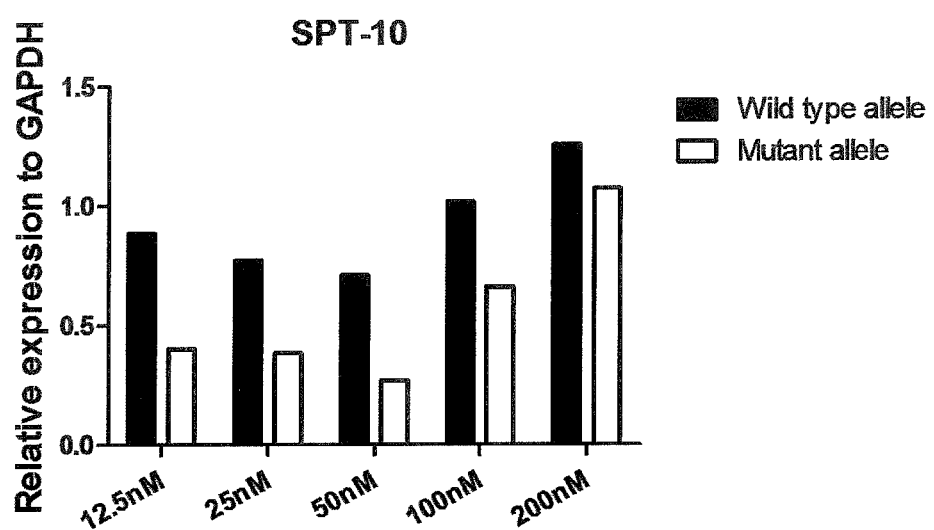
FIG. 6: Dose response study of SPT-10 the patient's fibroblasts. Dosages ranged from 12.5 nM to 200 nM. The expression of the wild type and mutant allele was measured by quantitative allele-specific real-time PCR.

A dose response experiment was performed on SPT-10 in the patient skin fibroblasts. A range between 12.5 nM and 200 nM was examined. Concentration as low as 12.5 nM gave the best efficiency in suppressing the expression of the mutant allele and preserving the expression of the wild type allele. (FIG. 6)

Figure 2:
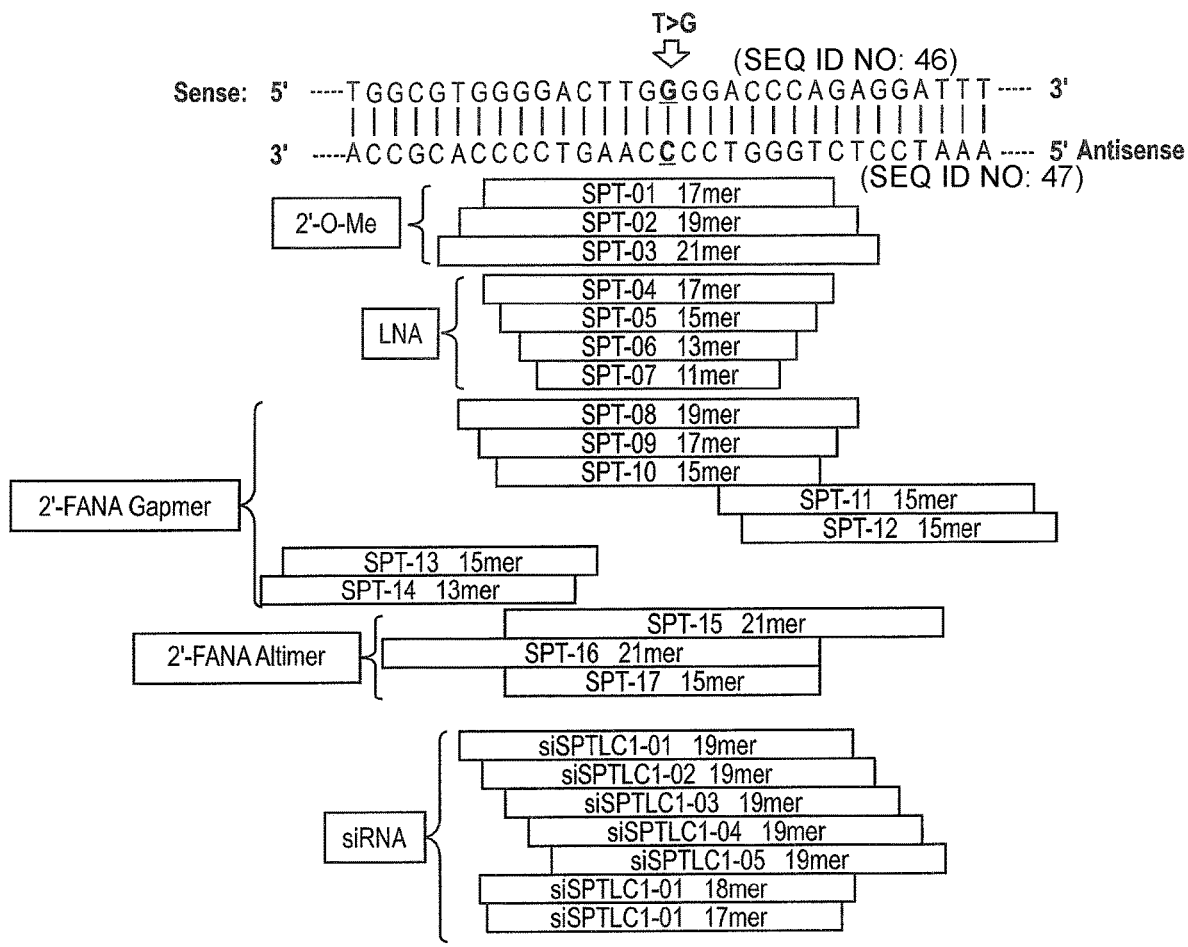
FIG. 2: Design of AONs and siRNAs targeting to the c.399T>G mutation.

Seven siRNA sequences were designed to target the c.399T>G mutant residue and flanking sequences (Table 1 and FIG. 2). Sanger sequencing and quantitative real-time PCR showed that none of the siRNAs gave any significant suppression of the mutant allele.

| Name | Type, chemistry and design | Length (bp) | Sequence |
|---|---|---|---|
| SPT-01 | AON 2'O-Me gapmer | 17 | [CUGGG]T*C*C*C\*C*A*A* [GUCCC] (SEQ ID NO: 1) |
| SPT-02 | AON 2'O-Me gapmer | 19 | [UCUGG] G*T*C*C*C\*C*A*A*G* [UCCCC] (SEQ ID NO: 12) |
| SPT-03 | AON 2'O-Me gapmer | 21 | [CUCUGG] G*T*C*C*C\*C*A*A*G* [UCCCCA] (SEQ ID NO: 13) |
| SPT-04 | AON LNA gapmer | 17 | {CUG} G*G*T*C*C*C\*C*A*A*G*T* {CCC} (SEQ ID NO: 14) |
| SPT-05 | AON LNA gapmer | 15 | {UGG}G*T*C*C*C\*C*A*A*G* {UCC} (SEQ ID NO: 15) |
| SPT-06 | AON LNA gapmer | 13 | {GGG}T*C*C*C\*C*A*A*{GUC} (SEQ ID NO: 16) |
| SPT-07 | AON LNA gapmer | 11 | {GGU}C*C*C*C\*A*{AGU} (SEQ ID NO: 17) |
| SPT-08 | AON FANA gapmer | 19 | (UCUGG) G*T*C*C*C\*C*A*A*G* (UCCCC) (SEQ ID NO: 18) |
| SPT-09 | AON FANA gapmer | 17 | (CUGGG)T*C*C*C\*C*A*A* (GUCCC) (SEQ ID NO: 19) |
| SPT-10 | AON FANA gapmer | 15 | (UGGGU)C*C*C\*C*A*(AGUCC) (SEQ ID NO: 2) |
| SPT-11 | AON FANA gapmer | 15 | (CCCCA)A*G*T*C*C*(CCACG) (SEQ ID NO: 20) |
| SPT-12 | AON FANA gapmer | 15 | (GTCCC)C*A*A*G*T*(CCCCA) (SEQ ID NO: 21) |
| SPT-13 | AON FANA gapmer | 15 | (CUCUG)G*G*T*C*C*(CCAAG) (SEQ ID NO: 22) |
| SPT-14 | AON FANA gapmer | 15 | (UCCUC)T*G*G*T*(CCCCA) (SEQ ID NO: 23) |
| SPT-15 | AON FANA Altimer | 21 | (UGG)G*T*C*(CCC)A*A*G* (UCC)C*C*A*(CGC) (SEQ ID NO: 24) |
| SPT-16 | AON FANA Altimer | 21 | (AUC)C*T*C*(UGG)G*T*C* (CCC)A*A*G*(UCC) (SEQ ID NO: 25) |
| SPT-17 | AON FANA Altimer | 15 | (UGG)G*T*C*(CCC)A*A*G* (UCC) (SEQ ID NO: 3) |
| siSPTLC1-1 | siRNA | 19 | Sense: GUGGGGACUUGGGGACCCA (SEQ ID NO: 26) Antisense: TGGGTCCCCAAGTCCCCAC (SEQ ID NO: 27) |
| siSPTLC1-2 | siRNA | 19 | Sense: UGGGGACUUGGGGACCCAG (SEQ ID NO: 28) Antisense: CTGGGTCCCCAAGTCCCCA (SEQ ID NO: 29) |
| siSPTLC1-3 | siRNA | 19 | Sense: GGGGACUUGGGGACCCAGA (SEQ ID NO: 30) Antisense: TCTGGGTCCCCAAGTCCCC (SEQ ID NO: 31) |
| siSPTLC1-4 | siRNA | 19 | Sense: GGGACUUGGGGACCCAGAG (SEQ ID NO: 32) Antisense: CTCTGGGTCCCCAAGTCCC (SEQ ID NO: 33) |
| siSPTLC1-5 | siRNA | 19 | Sense: GGACUUGGGGACCCAGAGG (SEQ ID NO: 34) Antisense: CCTCTGGGTCCCCAAGTCC (SEQ ID NO: 35) |
| siSPTLC1-6 | siRNA | 18 | Sense: GGGACUUGGGGACCCAGA (SEQ ID NO: 36) Antisense: TCTGGGTCCCCAAGTCCC (SEQ ID NO: 37) |
| siSPTLC1-7 | siRNA | 17 | Sense: GGGACUUGGGGACCCAG (SEQ ID NO: 38) Antisense: CTGGGTCCCCAAGTCCC (SEQ ID NO: 39) |

Note: * indicates phosphorothioated DNA backbone; [n] is 2'O-Me, {n} is LNA and (n) is 2'FANA RNA modification. The locus of c.399T > G mutation is in bold and underlined.

The invention claimed is:

1. An oligonucleotide that suppresses the expression of an allele carrying a dominant mutation that causes hereditary sensory neuropathy type I (HSN1), wherein the suppression takes place through hybridisation of said oligonucleotide to the DNA of said allele or to an RNA transcript of said allele, and which either does not suppress the expression of a wild-type allele not containing the dominant mutation or suppresses the expression of said wild-type allele to a lesser extent than it suppresses the expression of the dominant mutant allele, wherein the dominant mutation is in the serine palmitoyltransferase long chain subunit 1 (SPTLC1) gene, and wherein (i) the oligonucleotide is double-stranded; (ii) the oligonucleotide is a single-stranded antisense oligonucleotide (AON) comprising both DNA and RNA bases; or (iii) the oligonucleotide is a guide RNA comprising a guide sequence that hybridises to the site of said dominant mutation and targets a CRISPR-Cas enzyme to said site.

2. The oligonucleotide of claim 1 that hybridises to the site of said dominant mutation within the allele.

3. The oligonucleotide of claim 1 that hybridises to a site within the dominant mutant allele that is not the site of said dominant mutation but is also polymorphic and distinguishable between the dominant mutant allele and the wild-type allele, optionally wherein the site is a single nucleotide polymorphism (SNP) site.

4. The oligonucleotide of claim 1 wherein the dominant mutation is at: position 399, wherein T is mutated to G compared to the wild-type SPTLC1 gene; position 398, wherein G is mutated to A compared to the wild-type SPTLC1 gene; position 431, wherein T is mutated to A compared to the wild-type SPTLC1 gene; position 992, wherein C is mutated to T compared to the wild-type SPTLC1 gene; position 1055, wherein C is mutated to T compared to the wild-type SPTLC1 gene; or position 1160, wherein G is mutated to C compared to the wild-type SPTLC1 gene.

5. The oligonucleotide of claim 1 (ii) which is a gapmer or altimer.

6. The oligonucleotide of claim 1 (ii), wherein (i) some or all of the DNA bases have a phosphorothioated backbone and/or (ii) some or all of the RNA bases are 2'-O-Methyl (2'O-Me), locked nucleic acid (LNA) bases or 2'-deoxy-2'-fluorobeta-D-arabinonucleic acid (2'FANA) RNA bases.

7. The oligonucleotide of claim 6 (ii) which is a 2'O-Me gapmer, 2'FANA gapmer or 2'FANA altimer.

8. The oligonucleotide of claim 1 which is 10-25 nucleotides long.

9. The oligonucleotide of claim 1 (ii), wherein the AON has a sequence of any one of the following:

[CUGGG]TCCCCAA[GUCCC];  (SEQ ID NO: 1)

<UGGGU>CCCCA<AGUCC>;  (SEQ ID NO: 2)

<UGG>GTC<CCC>AAG<UCC>;  (SEQ ID NO: 3)

wherein [ ] denotes a 2'O-Me RNA base, and < > denotes a 2'FANA RNA base.

10. The oligonucleotide of claim 1 (i) which is a double-stranded RNA molecule.

11. The double-stranded oligonucleotide of claim 10 which is a siRNA.

12. The oligonucleotide of claim 9 which is an shRNA having a hairpin structure.

13. A pharmaceutical composition comprising the oligonucleotide of claim 1, together with a pharmaceutically acceptable carrier or excipient.

14. A method of treating HSN1 comprising administering an effective amount of the oligonucleotide of claim 1 to a subject suffering from HSN1.

* * * * *

SEQUENCE LISTING

<160> NUMBER OF SEQ ID NOS: 48

<210> SEQ ID NO 1
<211> LENGTH: 17
<212> TYPE: DNA
<213> ORGANISM: Artificial Sequence
<220> FEATURE:
<223> OTHER INFORMATION: AON 2'O-Me gapmer SPT-01
<220> FEATURE:
<221> NAME/KEY: misc_feature
<222> LOCATION: (1)..(5)
<223> OTHER INFORMATION: 2'O-Me
<220> FEATURE:

```
<221> NAME/KEY: misc_feature
<222> LOCATION: (6)..(12)
<223> OTHER INFORMATION: phosphorothioated DNA
<220> FEATURE:
<221> NAME/KEY: misc_feature
<222> LOCATION: (13)..(17)
<223> OTHER INFORMATION: 2'O-Me

<400> SEQUENCE: 1
cugggtcccc aagucccc                                                     17

<210> SEQ ID NO 2
<211> LENGTH: 15
<212> TYPE: DNA
<213> ORGANISM: Artificial Sequence
<220> FEATURE:
<223> OTHER INFORMATION: AON FANA gapmer SPT-10
<220> FEATURE:
<221> NAME/KEY: misc_feature
<222> LOCATION: (1)..(5)
<223> OTHER INFORMATION: 2'FANA RNA
<220> FEATURE:
<221> NAME/KEY: misc_feature
<222> LOCATION: (6)..(10)
<223> OTHER INFORMATION: phosphorothioated DNA
<220> FEATURE:
<221> NAME/KEY: misc_feature
<222> LOCATION: (11)..(15)
<223> OTHER INFORMATION: 2'FANA RNA

<400> SEQUENCE: 2
ugggucccca agucc                                                        15

<210> SEQ ID NO 3
<211> LENGTH: 15
<212> TYPE: DNA
<213> ORGANISM: Artificial Sequence
<220> FEATURE:
<223> OTHER INFORMATION: AON FANA altimer SPT-17
<220> FEATURE:
<221> NAME/KEY: misc_feature
<222> LOCATION: (1)..(3)
<223> OTHER INFORMATION: 2'FANA RNA
<220> FEATURE:
<221> NAME/KEY: misc_feature
<222> LOCATION: (4)..(6)
<223> OTHER INFORMATION: phosphorothioated DNA
<220> FEATURE:
<221> NAME/KEY: misc_feature
<222> LOCATION: (7)..(9)
<223> OTHER INFORMATION: 2'FANA RNA
<220> FEATURE:
<221> NAME/KEY: misc_feature
<222> LOCATION: (10)..(12)
<223> OTHER INFORMATION: phosphorothioated DNA
<220> FEATURE:
<221> NAME/KEY: misc_feature
<222> LOCATION: (13)..(15)
<223> OTHER INFORMATION: 2'FANA RNA

<400> SEQUENCE: 3
ugggtcccca agucc                                                        15

<210> SEQ ID NO 4
<211> LENGTH: 19
<212> TYPE: DNA
<213> ORGANISM: Artificial Sequence
<220> FEATURE:
<223> OTHER INFORMATION: forward primer

<400> SEQUENCE: 4
aacatcgttt caggccctc                                                    19
```

```
<210> SEQ ID NO 5
<211> LENGTH: 20
<212> TYPE: DNA
<213> ORGANISM: Artificial Sequence
<220> FEATURE:
<223> OTHER INFORMATION: reverse primer

<400> SEQUENCE: 5
gcaaagcagg cagctctatc                                                    20

<210> SEQ ID NO 6
<211> LENGTH: 18
<212> TYPE: DNA
<213> ORGANISM: Artificial Sequence
<220> FEATURE:
<223> OTHER INFORMATION: forward primer

<400> SEQUENCE: 6
tatggcgtgg ggacttgt                                                      18

<210> SEQ ID NO 7
<211> LENGTH: 20
<212> TYPE: DNA
<213> ORGANISM: Artificial Sequence
<220> FEATURE:
<223> OTHER INFORMATION: reverse primer

<400> SEQUENCE: 7
actggctatg gtggcaaatc                                                    20

<210> SEQ ID NO 8
<211> LENGTH: 18
<212> TYPE: DNA
<213> ORGANISM: Artificial Sequence
<220> FEATURE:
<223> OTHER INFORMATION: forward primer

<400> SEQUENCE: 8
tatggcgtgg ggacttgg                                                      18

<210> SEQ ID NO 9
<211> LENGTH: 20
<212> TYPE: DNA
<213> ORGANISM: Artificial Sequence
<220> FEATURE:
<223> OTHER INFORMATION: reverse primer

<400> SEQUENCE: 9
actggctatg gtggcaaatc                                                    20

<210> SEQ ID NO 10
<211> LENGTH: 20
<212> TYPE: DNA
<213> ORGANISM: Artificial Sequence
<220> FEATURE:
<223> OTHER INFORMATION: forward primer

<400> SEQUENCE: 10
ttgaggtcaa tgaagggtc                                                     20

<210> SEQ ID NO 11
<211> LENGTH: 20
<212> TYPE: DNA
<213> ORGANISM: Artificial Sequence
<220> FEATURE:
```

```
<223> OTHER INFORMATION: reverse primer

<400> SEQUENCE: 11
gaaggtgaag gtcggagtca                                                    20

<210> SEQ ID NO 12
<211> LENGTH: 19
<212> TYPE: DNA
<213> ORGANISM: Artificial Sequence
<220> FEATURE:
<223> OTHER INFORMATION: AON 2'O-Me gapmer SPT-02
<220> FEATURE:
<221> NAME/KEY: misc_feature
<222> LOCATION: (1)..(5)
<223> OTHER INFORMATION: 2'O-Me
<220> FEATURE:
<221> NAME/KEY: misc_feature
<222> LOCATION: (6)..(14)
<223> OTHER INFORMATION: phosphorothioated DNA
<220> FEATURE:
<221> NAME/KEY: misc_feature
<222> LOCATION: (15)..(19)
<223> OTHER INFORMATION: 2'O-Me

<400> SEQUENCE: 12
ucugggtccc caagucccc                                                     19

<210> SEQ ID NO 13
<211> LENGTH: 21
<212> TYPE: DNA
<213> ORGANISM: Artificial Sequence
<220> FEATURE:
<223> OTHER INFORMATION: AON 2'O-Me gapmer SPT-03
<220> FEATURE:
<221> NAME/KEY: misc_feature
<222> LOCATION: (1)..(6)
<223> OTHER INFORMATION: 2'O-Me
<220> FEATURE:
<221> NAME/KEY: misc_feature
<222> LOCATION: (7)..(15)
<223> OTHER INFORMATION: phosphorothioated DNA
<220> FEATURE:
<221> NAME/KEY: misc_feature
<222> LOCATION: (16)..(21)
<223> OTHER INFORMATION: 2'O-Me

<400> SEQUENCE: 13
cucugggtcc ccaagucccc a                                                  21

<210> SEQ ID NO 14
<211> LENGTH: 17
<212> TYPE: DNA
<213> ORGANISM: Artificial Sequence
<220> FEATURE:
<223> OTHER INFORMATION: AON LNA gapmer SPT-04
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (4)..(14)
<223> OTHER INFORMATION: phosphorothioated DNA
<220> FEATURE:
<221> NAME/KEY: misc_feature
<222> LOCATION: (15)..(17)
<223> OTHER INFORMATION: LNA

<400> SEQUENCE: 14
cugggtcccc aagtccc                                                       17
```

```
<210> SEQ ID NO 15
<211> LENGTH: 15
<212> TYPE: DNA
<213> ORGANISM: Artificial Sequence
<220> FEATURE:
<223> OTHER INFORMATION: AON LNA gapmer SPT-05
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (4)..(12)
<223> OTHER INFORMATION: phosphorothioated DNA
<220> FEATURE:
<221> NAME/KEY: misc_feature
<222> LOCATION: (13)..(15)
<223> OTHER INFORMATION: LNA

<400> SEQUENCE: 15
ugggtcccca agucc                                                          15

<210> SEQ ID NO 16
<211> LENGTH: 13
<212> TYPE: DNA
<213> ORGANISM: Artificial Sequence
<220> FEATURE:
<223> OTHER INFORMATION: AON LNA gapmer SPT-06
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (4)..(10)
<223> OTHER INFORMATION: phosphorothioated DNA
<220> FEATURE:
<221> NAME/KEY: misc_feature
<222> LOCATION: (11)..(13)
<223> OTHER INFORMATION: LNA

<400> SEQUENCE: 16
gggtccccaa guc                                                            13

<210> SEQ ID NO 17
<211> LENGTH: 11
<212> TYPE: DNA
<213> ORGANISM: Artificial Sequence
<220> FEATURE:
<223> OTHER INFORMATION: AON LNA gapmer SPT-07
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (4)..(8)
<223> OTHER INFORMATION: phosphorothioated DNA
<220> FEATURE:
<221> NAME/KEY: misc_feature
<222> LOCATION: (9)..(11)
<223> OTHER INFORMATION: LNA

<400> SEQUENCE: 17
gguccccaag u                                                              11

<210> SEQ ID NO 18
<211> LENGTH: 19
<212> TYPE: DNA
<213> ORGANISM: Artificial Sequence
<220> FEATURE:
<223> OTHER INFORMATION: AON FANA gapmer SPT-08
<220> FEATURE:
```

```
<221> NAME/KEY: misc_feature
<222> LOCATION: (1)..(5)
<223> OTHER INFORMATION: 2'FANA RNA
<220> FEATURE:
<221> NAME/KEY: misc_feature
<222> LOCATION: (6)..(14)
<223> OTHER INFORMATION: phosphorothioated DNA
<220> FEATURE:
<221> NAME/KEY: misc_feature
<222> LOCATION: (15)..(19)
<223> OTHER INFORMATION: 2'FANA RNA

<400> SEQUENCE: 18
ucugggtccc caaguccccc                                              19

<210> SEQ ID NO 19
<211> LENGTH: 17
<212> TYPE: DNA
<213> ORGANISM: Artificial Sequence
<220> FEATURE:
<223> OTHER INFORMATION: AON FANA gapmer SPT-09
<220> FEATURE:
<221> NAME/KEY: misc_feature
<222> LOCATION: (1)..(5)
<223> OTHER INFORMATION: 2'FANA RNA
<220> FEATURE:
<221> NAME/KEY: misc_feature
<222> LOCATION: (6)..(12)
<223> OTHER INFORMATION: phosphorothioated DNA
<220> FEATURE:
<221> NAME/KEY: misc_feature
<222> LOCATION: (13)..(17)
<223> OTHER INFORMATION: 2'FANA RNA

<400> SEQUENCE: 19
cugggtcccc aaguccc                                                 17

<210> SEQ ID NO 20
<211> LENGTH: 15
<212> TYPE: DNA
<213> ORGANISM: Artificial Sequence
<220> FEATURE:
<223> OTHER INFORMATION: AON FANA gapmer SPT-11
<220> FEATURE:
<221> NAME/KEY: misc_feature
<222> LOCATION: (1)..(5)
<223> OTHER INFORMATION: 2'FANA RNA
<220> FEATURE:
<221> NAME/KEY: misc_feature
<222> LOCATION: (6)..(10)
<223> OTHER INFORMATION: phosphorothioated DNA
<220> FEATURE:
<221> NAME/KEY: misc_feature
<222> LOCATION: (11)..(15)
<223> OTHER INFORMATION: 2'FANA RNA

<400> SEQUENCE: 20
ccccaagtcc ccacg                                                   15

<210> SEQ ID NO 21
<211> LENGTH: 15
<212> TYPE: DNA
<213> ORGANISM: Artificial Sequence
<220> FEATURE:
<223> OTHER INFORMATION: AON FANA gapmer SPT-12
<220> FEATURE:
<221> NAME/KEY: misc_feature
<222> LOCATION: (1)..(5)
<223> OTHER INFORMATION: 2'FANA RNA
<220> FEATURE:
<221> NAME/KEY: misc_feature
<222> LOCATION: (6)..(10)
<223> OTHER INFORMATION: phosphorothioated DNA
```

```
<220> FEATURE:
<221> NAME/KEY: misc_feature
<222> LOCATION: (11)..(15)
<223> OTHER INFORMATION: 2'FANA RNA

<400> SEQUENCE: 21
gtccccaagt cccca                                                      15

<210> SEQ ID NO 22
<211> LENGTH: 15
<212> TYPE: DNA
<213> ORGANISM: Artificial Sequence
<220> FEATURE:
<223> OTHER INFORMATION: AON FANA gapmer SPT-13
<220> FEATURE:
<221> NAME/KEY: misc_feature
<222> LOCATION: (1)..(5)
<223> OTHER INFORMATION: 2'FANA RNA
<220> FEATURE:
<221> NAME/KEY: misc_feature
<222> LOCATION: (6)..(10)
<223> OTHER INFORMATION: phosphorothioated DNA
<220> FEATURE:
<221> NAME/KEY: misc_feature
<222> LOCATION: (11)..(15)
<223> OTHER INFORMATION: 2'FANA RNA

<400> SEQUENCE: 22
cucugggtcc ccaag                                                      15

<210> SEQ ID NO 23
<211> LENGTH: 15
<212> TYPE: DNA
<213> ORGANISM: Artificial Sequence
<220> FEATURE:
<223> OTHER INFORMATION: AON FANA gapmer SPT-14
<220> FEATURE:
<221> NAME/KEY: misc_feature
<222> LOCATION: (1)..(5)
<223> OTHER INFORMATION: 2'FANA RNA
<220> FEATURE:
<221> NAME/KEY: misc_feature
<222> LOCATION: (6)..(10)
<223> OTHER INFORMATION: phosphorothioated DNA
<220> FEATURE:
<221> NAME/KEY: misc_feature
<222> LOCATION: (11)..(15)
<223> OTHER INFORMATION: 2'FANA RNA

<400> SEQUENCE: 23
uccuctgggt cccca                                                      15

<210> SEQ ID NO 24
<211> LENGTH: 21
<212> TYPE: DNA
<213> ORGANISM: Artificial Sequence
<220> FEATURE:
<223> OTHER INFORMATION: AON FANA altimer SPT-15
<220> FEATURE:
<221> NAME/KEY: misc_feature
<222> LOCATION: (1)..(3)
<223> OTHER INFORMATION: 2'FANA RNA
<220> FEATURE:
<221> NAME/KEY: misc_feature
<222> LOCATION: (4)..(6)
<223> OTHER INFORMATION: phosphorothioated DNA
<220> FEATURE:
<221> NAME/KEY: misc_feature
<222> LOCATION: (7)..(9)
<223> OTHER INFORMATION: 2'FANA RNA
<220> FEATURE:
<221> NAME/KEY: misc_feature
<222> LOCATION: (10)..(12)
```

```
<223> OTHER INFORMATION: phosphorothioated DNA
<220> FEATURE:
<221> NAME/KEY: misc_feature
<222> LOCATION: (13)..(15)
<223> OTHER INFORMATION: 2'FANA RNA
<220> FEATURE:
<221> NAME/KEY: misc_feature
<222> LOCATION: (16)..(18)
<223> OTHER INFORMATION: phosphorothioated DNA
<220> FEATURE:
<221> NAME/KEY: misc_feature
<222> LOCATION: (19)..(21)
<223> OTHER INFORMATION: 2'FANA RNA

<400> SEQUENCE: 24
ugggtcccca agucccacg c                                                21

<210> SEQ ID NO 25
<211> LENGTH: 21
<212> TYPE: DNA
<213> ORGANISM: Artificial Sequence
<220> FEATURE:
<223> OTHER INFORMATION: AON FANA altimer SPT-16
<220> FEATURE:
<221> NAME/KEY: misc_feature
<222> LOCATION: (1)..(3)
<223> OTHER INFORMATION: 2'FANA RNA
<220> FEATURE:
<221> NAME/KEY: misc_feature
<222> LOCATION: (4)..(6)
<223> OTHER INFORMATION: phosphorothioated DNA
<220> FEATURE:
<221> NAME/KEY: misc_feature
<222> LOCATION: (7)..(9)
<223> OTHER INFORMATION: 2'FANA RNA
<220> FEATURE:
<221> NAME/KEY: misc_feature
<222> LOCATION: (10)..(12)
<223> OTHER INFORMATION: phosphorothioated DNA
<220> FEATURE:
<221> NAME/KEY: misc_feature
<222> LOCATION: (13)..(15)
<223> OTHER INFORMATION: 2'FANA RNA
<220> FEATURE:
<221> NAME/KEY: misc_feature
<222> LOCATION: (16)..(18)
<223> OTHER INFORMATION: phosphorothioated DNA
<220> FEATURE:
<221> NAME/KEY: misc_feature
<222> LOCATION: (19)..(21)
<223> OTHER INFORMATION: 2'FANA RNA

<400> SEQUENCE: 25
auccucuggg tccccaaguc c                                               21

<210> SEQ ID NO 26
<211> LENGTH: 19
<212> TYPE: DNA
<213> ORGANISM: Artificial Sequence
<220> FEATURE:
<223> OTHER INFORMATION: siSPTLC1-1 sense strand

<400> SEQUENCE: 26 gugggggacuu ggggaccca                                                 19

<210> SEQ ID NO 27
<211> LENGTH: 19
<212> TYPE: DNA
<213> ORGANISM: Artificial Sequence
<220> FEATURE:
<223> OTHER INFORMATION: siSPTLC1-1 antisense strand

<400> SEQUENCE: 27
```
tgggtcccca agtccccac                                                19

<210> SEQ ID NO 28
<211> LENGTH: 19
<212> TYPE: DNA
<213> ORGANISM: Artificial Sequence
<220> FEATURE:
<223> OTHER INFORMATION: siSPTLC1-2 sense strand

<400> SEQUENCE: 28 ugggga cuug gggacccag                                               19

<210> SEQ ID NO 29
<211> LENGTH: 19
<212> TYPE: DNA
<213> ORGANISM: Artificial Sequence
<220> FEATURE:
<223> OTHER INFORMATION: siSPTLC1-2 antisense strand

<400> SEQUENCE: 29
ctgggtcccc aagtcccca                                                19

<210> SEQ ID NO 30
<211> LENGTH: 19
<212> TYPE: DNA
<213> ORGANISM: Artificial Sequence
<220> FEATURE:
<223> OTHER INFORMATION: siSPTLC1-3 sense strand

<400> SEQUENCE: 30
ggggacuugg ggacccaga                                                19

<210> SEQ ID NO 31
<211> LENGTH: 19
<212> TYPE: DNA
<213> ORGANISM: Artificial Sequence
<220> FEATURE:
<223> OTHER INFORMATION: siSPTLC1-3 antisense strand

<400> SEQUENCE: 31
tctgggtccc caagtcccc                                                19

<210> SEQ ID NO 32
<211> LENGTH: 19
<212> TYPE: DNA
<213> ORGANISM: Artificial Sequence
<220> FEATURE:
<223> OTHER INFORMATION: siSPTLC1-4 sense strand

<400> SEQUENCE: 32
gggacuuggg gacccagag                                                19

<210> SEQ ID NO 33
<211> LENGTH: 19
<212> TYPE: DNA
<213> ORGANISM: Artificial Sequence
<220> FEATURE:
<223> OTHER INFORMATION: siSPTLC1-4 antisense strand

<400> SEQUENCE: 33
ctctgggtcc ccaagtccc                                                19

<210> SEQ ID NO 34
<211> LENGTH: 19
<212> TYPE: DNA

```
<213> ORGANISM: Artificial Sequence
<220> FEATURE:
<223> OTHER INFORMATION: siSPTLC1-5 sense strand

<400> SEQUENCE: 34
ggacuugggg acccagagg                                                    19

<210> SEQ ID NO 35
<211> LENGTH: 19
<212> TYPE: DNA
<213> ORGANISM: Artificial Sequence
<220> FEATURE:
<223> OTHER INFORMATION: siSPTLC1-5 antisense strand

<400> SEQUENCE: 35
cctctgggtc cccaagtcc                                                    19

<210> SEQ ID NO 36
<211> LENGTH: 18
<212> TYPE: DNA
<213> ORGANISM: Artificial Sequence
<220> FEATURE:
<223> OTHER INFORMATION: siSPTLC1-6 sense strand

<400> SEQUENCE: 36
gggacuuggg gacccaga                                                     18

<210> SEQ ID NO 37
<211> LENGTH: 18
<212> TYPE: DNA
<213> ORGANISM: Artificial Sequence
<220> FEATURE:
<223> OTHER INFORMATION: siSPTLC1-6 antisense strand

<400> SEQUENCE: 37
tctgggtccc caagtccc                                                     18

<210> SEQ ID NO 38
<211> LENGTH: 17
<212> TYPE: DNA
<213> ORGANISM: Artificial Sequence
<220> FEATURE:
<223> OTHER INFORMATION: siSPTLC1-7 sense strand

<400> SEQUENCE: 38
gggacuuggg gacccag                                                      17

<210> SEQ ID NO 39
<211> LENGTH: 17
<212> TYPE: DNA
<213> ORGANISM: Artificial Sequence
<220> FEATURE:
<223> OTHER INFORMATION: siSPTLC1-7 antisense strand

<400> SEQUENCE: 39
ctgggtcccc aagtccc                                                      17

<210> SEQ ID NO 40
<211> LENGTH: 473
<212> TYPE: PRT
<213> ORGANISM: Homo sapiens

<400> SEQUENCE: 40

Met Ala Thr Ala Thr Glu Gln Trp Val Leu Val Glu Met Val Gln Ala
1               5                   10                  15
```

```
Leu Tyr Glu Ala Pro Ala Tyr His Leu Ile Leu Glu Gly Ile Leu Ile
             20                  25                  30

Leu Trp Ile Ile Arg Leu Leu Phe Ser Lys Thr Tyr Lys Leu Gln Glu
         35                  40                  45

Arg Ser Asp Leu Thr Val Lys Glu Lys Glu Glu Leu Ile Glu Glu Trp
 50                  55                  60

Gln Pro Glu Pro Leu Val Pro Pro Val Pro Lys Asp His Pro Ala Leu
 65                  70                  75                  80

Asn Tyr Asn Ile Val Ser Gly Pro Ser His Lys Thr Val Val Asn
                 85                  90                  95

Gly Lys Glu Cys Ile Asn Phe Ala Ser Phe Asn Phe Leu Gly Leu Leu
             100                 105                 110

Asp Asn Pro Arg Val Lys Ala Ala Leu Ala Ser Leu Lys Lys Tyr
             115                 120                 125

Gly Val Gly Thr Cys Gly Pro Arg Gly Phe Tyr Gly Thr Phe Asp Val
             130                 135                 140

His Leu Asp Leu Glu Asp Arg Leu Ala Lys Phe Met Lys Thr Glu Glu
145                 150                 155                 160

Ala Ile Ile Tyr Ser Tyr Gly Phe Ala Thr Ile Ala Ser Ala Ile Pro
                 165                 170                 175

Ala Tyr Ser Lys Arg Gly Asp Ile Val Phe Val Asp Arg Ala Ala Cys
             180                 185                 190

Phe Ala Ile Gln Lys Gly Leu Gln Ala Ser Arg Ser Asp Ile Lys Leu
             195                 200                 205

Phe Lys His Asn Asp Met Ala Asp Leu Glu Arg Leu Leu Lys Glu Gln
210                 215                 220

Glu Ile Glu Asp Gln Lys Asn Pro Arg Lys Ala Arg Val Thr Arg Arg
225                 230                 235                 240

Phe Ile Val Val Glu Gly Leu Tyr Met Asn Thr Gly Thr Ile Cys Pro
                 245                 250                 255

Leu Pro Glu Leu Val Lys Leu Lys Tyr Lys Tyr Lys Ala Arg Ile Phe
             260                 265                 270

Leu Glu Glu Ser Leu Ser Phe Gly Val Leu Gly Glu His Gly Arg Gly
             275                 280                 285

Val Thr Glu His Tyr Gly Ile Asn Ile Asp Asp Ile Asp Leu Ile Ser
             290                 295                 300

Ala Asn Met Glu Asn Ala Leu Ala Ser Ile Gly Gly Phe Cys Cys Gly
305                 310                 315                 320

Arg Ser Phe Val Ile Asp His Gln Arg Leu Ser Gly Gln Gly Tyr Cys
             325                 330                 335

Phe Ser Ala Ser Leu Pro Pro Leu Leu Ala Ala Ala Ile Glu Ala
             340                 345                 350

Leu Asn Ile Met Glu Glu Asn Pro Gly Ile Phe Ala Val Leu Lys Glu
             355                 360                 365

Lys Cys Gly Gln Ile His Lys Ala Leu Gln Gly Ile Ser Gly Leu Lys
             370                 375                 380

Val Val Gly Glu Ser Leu Ser Pro Ala Phe His Leu Gln Leu Glu Glu
385                 390                 395                 400

Ser Thr Gly Ser Arg Glu Gln Asp Val Arg Leu Leu Gln Glu Ile Val
                 405                 410                 415

Asp Gln Cys Met Asn Arg Ser Ile Ala Leu Thr Gln Ala Arg Tyr Leu
             420                 425                 430

Glu Lys Glu Glu Lys Cys Leu Pro Pro Pro Ser Ile Arg Val Val Val
```

435                 440                 445
Thr Val Glu Gln Thr Glu Glu Leu Glu Arg Ala Ala Ser Thr Ile
      450                 455                 460
Lys Glu Val Ala Gln Ala Val Leu Leu
465                 470

<210> SEQ ID NO 41
<211> LENGTH: 30
<212> TYPE: DNA
<213> ORGANISM: Homo sapiens

<400> SEQUENCE: 41
ggcgtgggga cttgtggacc cagaggattt                                30

<210> SEQ ID NO 42
<211> LENGTH: 31
<212> TYPE: DNA
<213> ORGANISM: Homo sapiens

<400> SEQUENCE: 42
tatggcacat ttgatgttca tttggatttg g                              31

<210> SEQ ID NO 43
<211> LENGTH: 24
<212> TYPE: DNA
<213> ORGANISM: Homo sapiens

<400> SEQUENCE: 43
aaaagtggtg ggggagtccc tttc                                      24

<210> SEQ ID NO 44
<211> LENGTH: 28
<212> TYPE: DNA
<213> ORGANISM: Homo sapiens

<400> SEQUENCE: 44
catcagcgac tttccggcca gggatact                                  28

<210> SEQ ID NO 45
<211> LENGTH: 27
<212> TYPE: DNA
<213> ORGANISM: Homo sapiens

<400> SEQUENCE: 45
cagcaattga ggccctcaac atcatgg                                   27

<210> SEQ ID NO 46
<211> LENGTH: 31
<212> TYPE: DNA
<213> ORGANISM: Artificial Sequence
<220> FEATURE:
<223> OTHER INFORMATION: Figure 2 sense strand

<400> SEQUENCE: 46
tggcgtgggg acttggggac ccagaggatt t                              31

<210> SEQ ID NO 47
<211> LENGTH: 31
<212> TYPE: DNA
<213> ORGANISM: Artificial Sequence
<220> FEATURE:
<223> OTHER INFORMATION: Figure 2 antisense strand

<400> SEQUENCE: 47

```
aaatcctctg ggtccccaag tccccacgcc a                                      31

<210> SEQ ID NO 48
<211> LENGTH: 13
<212> TYPE: DNA
<213> ORGANISM: Artificial Sequence
<220> FEATURE:
<223> OTHER INFORMATION: Figure 3A PCR product amplified from
      AON-treated fibroblasts

<400> SEQUENCE: 48
gacttgtgga ccc                                                          13
```